(12) United States Patent
Gross

(10) Patent No.: US 11,334,679 B2
(45) Date of Patent: May 17, 2022

(54) SYSTEM AND METHOD FOR OPTIMIZING A USER EXPERIENCE BASED ON PATIENT CONTEXT, USER ROLES, CURRENT WORKFLOW, AND DISPLAY PROXIMITY

(71) Applicant: KONINKLIJKE PHILIPS N.V., Eindhoven (NL)

(72) Inventor: Brian David Gross, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 506 days.

(21) Appl. No.: 16/318,169

(22) PCT Filed: Jul. 27, 2017

(86) PCT No.: PCT/EP2017/069075
§ 371 (c)(1),
(2) Date: Jan. 16, 2019

(87) PCT Pub. No.: WO2018/019959
PCT Pub. Date: Feb. 1, 2018

(65) Prior Publication Data
US 2019/0286844 A1 Sep. 19, 2019

Related U.S. Application Data

(60) Provisional application No. 62/367,746, filed on Jul. 28, 2016.

(51) Int. Cl.
*G16H 40/20* (2018.01)
*G06F 21/62* (2013.01)
(Continued)

(52) U.S. Cl.
CPC ........ *G06F 21/6245* (2013.01); *G06Q 50/22* (2013.01); *G16H 10/60* (2018.01);
(Continued)

(58) Field of Classification Search
USPC ............ 726/1, 2, 21, 36; 713/150, 163, 181; 380/255, 264, 276
See application file for complete search history.

(56) References Cited

U.S. PATENT DOCUMENTS

2006/0288095 A1* 12/2006 Torok ...................... G16H 40/20
709/223
2009/0079765 A1* 3/2009 Hoover ................. G06F 3/0481
345/660

(Continued)

FOREIGN PATENT DOCUMENTS

| JP | 10260666 A | 9/1998 |
|----|------------|--------|
| JP | 2003271276 A | 9/2003 |
| JP | 2013061923 A | 4/2013 |

*Primary Examiner* — Sharif E Ullah

(57) ABSTRACT

In a medical workspaces management method, a user identified in a users database (52) is authenticated. At a server computer (10), a virtual session is created including running instances (16) of a plurality of medical applications on the server computer with the instances associated with the authenticated user. Using at least one locating service (20), a current medical content presentation device (30, 32) is identified which is proximate to the authenticated user. At the server computer, a set of rules is applied to determine content of the instances to be presented. This content is pushed from the server computer to the current medical content presentation device. At the current medical content presentation device, the pushed content is presented on a display (40, 42) of the current medical content presentation device.

26 Claims, 3 Drawing Sheets

(51) Int. Cl.
*G16H 10/60* (2018.01)
*H04L 29/06* (2006.01)
*H04L 67/12* (2022.01)
*H04L 67/141* (2022.01)
*H04L 67/52* (2022.01)
*H04L 67/55* (2022.01)
*G16H 80/00* (2018.01)
*G06Q 50/22* (2018.01)
*H04W 4/33* (2018.01)
*H04W 12/06* (2021.01)
*G06Q 10/10* (2012.01)
*H04L 67/14* (2022.01)
*H04W 12/63* (2021.01)

(52) U.S. Cl.
CPC ............ *G16H 40/20* (2018.01); *G16H 80/00* (2018.01); *H04L 63/08* (2013.01); *H04L 63/105* (2013.01); *H04L 63/107* (2013.01); *H04L 67/12* (2013.01); *H04L 67/141* (2013.01); *H04L 67/18* (2013.01); *H04L 67/26* (2013.01); *G06Q 10/10* (2013.01); *H04L 67/14* (2013.01); *H04W 4/33* (2018.02); *H04W 12/06* (2013.01); *H04W 12/63* (2021.01)

(56) References Cited

U.S. PATENT DOCUMENTS

| | | | |
|---|---|---|---|
| 2013/0205373 A1* | 8/2013 | Jaudon | H04W 4/06 726/4 |
| 2015/0019260 A1* | 1/2015 | Samani | G16H 10/60 705/3 |
| 2015/0302179 A1* | 10/2015 | Rheault | G16Z 99/00 705/2 |

* cited by examiner

SYSTEM AND METHOD FOR OPTIMIZING A USER EXPERIENCE BASED ON PATIENT CONTEXT, USER ROLES, CURRENT WORKFLOW, AND DISPLAY PROXIMITY

CROSS REFERENCE TO RELATED APPLICATIONS

This application is the U.S. National Phase application under 35 U.S.C. § 371 of International Application No. PCT/EP2017/069075 filed Jul. 27, 2017, published as WO 2018/019959 on Feb. 1, 2018, which claims the benefit of U.S. Provisional Patent Application No. 62/367,746 filed Jul. 28, 2016. These applications are hereby incorporated by reference herein.

FIELD

The following relates generally to medical information systems, medical display devices, patient monitors, medical care collaboration systems, and related arts.

BACKGROUND

In clinical information technology (IT) systems, user authentication is generally required to use a device that accesses patient medical information, or to use a particular application or system that contains or accesses patient data, such as a Health Information System (HIS), Picture Archiving and Communication System (PACS), cardiovascular information system (CVIS), or so forth. Authentication protects privacy of patient medical information as commonly required by jurisdictional laws or rules such as the Health Insurance Portability and Accountability Act (HIPAA) governing in the United States. As a consequence, a doctor or other medical personnel operating "on the go" in a hospital or other medical institution may spend significant amounts of time logging into devices and applications or systems as he or she moves between patient rooms, laboratories, or other locations. At each location, additional time may be lost as each application loads onto a given device, and as the records for a particular patient are loaded into the application. Such problems are enhanced in certain situations, such as at round change when an outgoing medical work shift is transferring current patient status information to an incoming medical work shift. Other issues can arise. For example, even with authentication, medical information may be improperly or undesirably conveyed if a user has logged in and is displaying sensitive patient information when non-medical personnel enter the room.

More generally, such user authentication and application workspace management systems allow a user to open a "desktop" experience that can follow the user as he or she move to different work stations (e.g. patient rooms, nurses' stations, laboratories, et cetera). These systems may have safeguards such as filtering the resources available to the user depending on where they logged (e.g. inside versus outside a protected environment), and/or manage how long a user can remain logged on before they are automatically logged off.

The following discloses a new and improved systems and methods.

SUMMARY

In one disclosed aspect, a non-transitory storage medium stores instructions readable and executable by a server computer to perform a medical workspaces management method comprising: authenticating a user identified in a users database whereby the user becomes an authenticated user; creating a virtual session including running instances of a plurality of medical applications on the server computer with the instances associated with the authenticated user; identifying a current medical content presentation device proximate to or accessed by the authenticated user; applying a set of rules to determine content of the instances to be presented; and pushing the content to be presented from the server computer to the current medical content presentation device for presentation at the current medical content presentation device.

In another disclosed aspect, a medical workspaces management device comprises a server computer and a non-transitory storage medium that stores instructions readable and executable by the server computer to perform a medical workspaces management method. The method includes: authenticating a user identified in a users database whereby the user becomes an authenticated user; after completion of the authenticating, creating a virtual session including running instances of a plurality of medical applications on the server computer with the instances associated with the authenticated user; tracking a current location of the authenticated user using at least one locating service; identifying a current medical content presentation device based on proximity of the current location of the authenticated user to the current medical content presentation device; applying a set of rules to determine content of the instances to be presented; and pushing the content to be presented from the server computer to the current medical content presentation device for presentation at the current medical content presentation device.

In another disclosed aspect, a medical workspaces management method is disclosed. At a server computer, a user identified in a users database is authenticated whereby the user becomes an authenticated user. At the server computer, a virtual session is created including running instances of a plurality of medical applications on the server computer with the instances associated with the authenticated user. Using at least one locating service, a current medical content presentation device is identified which is proximate to the authenticated user. At the server computer, a set of rules is applied to determine content of the instances to be presented. The content to be presented is pushed from the server computer to the current medical content presentation device. At the current medical content presentation device, the content pushed from the server computer is presented on a display of the current medical content presentation device.

One advantage resides in providing medical personnel with more efficient access to medical workflows and applications.

Another advantage resides in the control of which application and what part of the application is presented to the user based on clinical context.

Another advantage resides in establishing a common user context across a multitude of independent applications.

Another advantage resides in establishing a common patient or client context across a multitude of independent applications that have data for the patient or client.

Another advantage resides in providing contextual display of medical information based on location of the display.

Another advantage resides in providing contextual display of medical information based on persons present.

Another advantage resides in providing contextual display of medical information based on proximity of persons present to the device presenting the medical information.

Another advantage resides in providing improved security for patient information.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention. In drawings presenting log or service call data, certain identifying information has been redacted by use of superimposed redaction boxes.

DETAILED DESCRIPTION

Figure 1:
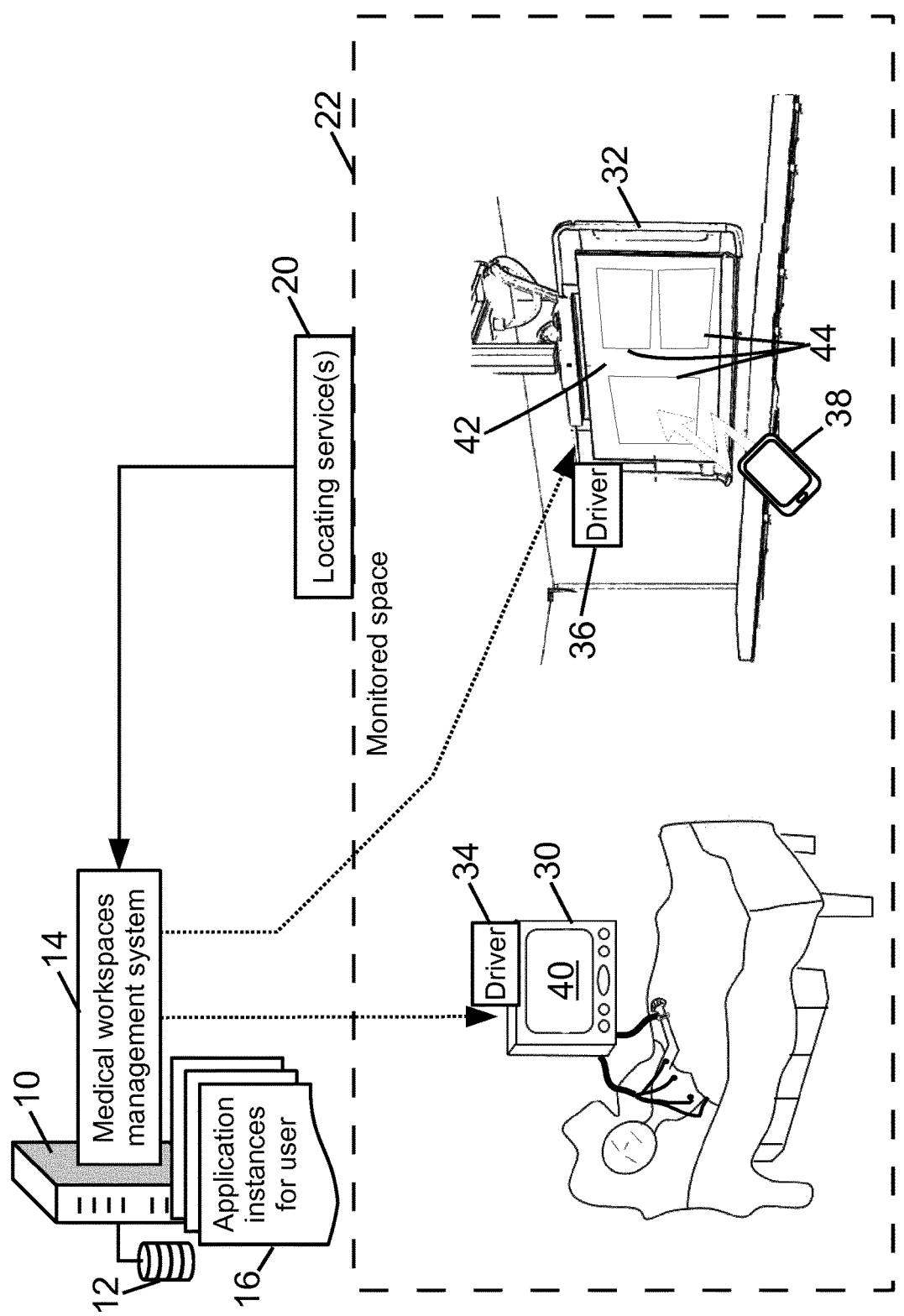
FIG. 1 diagrammatically shows an illustrative medical workspaces management system in context of portions of an illustrative medical facility.

In some medical workspaces management systems disclosed herein, a central server (which may be embodied as a single server computer or a cloud resource or other distributed computing resource) creates a set of virtual sessions for various applications a user (e.g. doctor) is authorized to use. These sessions are started either automatically when the doctor is scheduled to go on-service, or in response to the clinical user (e.g. a doctor, a nurse, a respiratory therapist and so forth) swiping an access badge or otherwise gaining access to the physical facility through a digital method or otherwise logging in. The virtual sessions are pushed to various medical content presentation devices (e.g. nurses' station terminals, bedside patient monitors, electronic whiteboards, and/or so forth) to display the content of the virtual sessions. In one approach, this is done in response to the doctor logging onto the medical content presentation device. In other embodiments, a real time location service (RTLS, or more generally one or more locating services of various spatial/temporal granularity) is used to track the doctor in real time as he makes rounds or otherwise moves about the hospital or other medical facility, and automatically logs the doctor into and out of medical content presentation devices as the doctor move into or out of proximity to these devices. In other embodiments, the proximity to the display is used to generate a view across the applications that is readable at the distance the user is from the display. Thus, for example, as the doctor enters a patient room an electronic white board may log the doctor in, retrieve the patient's medical record from a Health Information System (HIS), and display the medical record or salient portions thereof (e.g. cardiac-related information if the doctor is a cardiologist) on the white board and display the real time bedside monitor, and display the physician's schedule.

In some contemplated embodiments, if the locating service(s) include an RTLS has sufficient granularity to measure proximity of the doctor to the white board with sufficient accuracy, it can adjust display aspects such as font size and/or the amount of displayed informational content to adapt to the viewing distance. For large displays, multiple tiles or windows may be displayed, e.g. a different tile for each doctor present in order to display content for that doctor. In a further variant, each user's cellphone (or tablet computer or other mobile device) may be used as a user interfacing device to enable simultaneous user interfacing with the different tiles.

In some embodiments, the display content is tailored for multiple users in the same room by displaying information contextually based on the attendance. For example, if the identities of the users present at the same time in a patient room indicate that a shift change is occurring and incoming medical personnel are being briefed on the patient's condition by outgoing medical personnel, then the electronic white board may display medical information on the patient' current status. The displayed information may optionally be tailored to the specialties of the doctors in attendance. On the other hand, if persons are present who are not identified as users (and hence presumably are lay persons) or are positively identified as family or other lay persons, then the electronic white board may display soothing images or other non-medical information unless a user provides active inputs commanding the display of patient medical information.

With reference to FIG. 1, in an illustrative implementation, a central server computer 10 reads and executes instructions stored on a non-transitory storage medium 12 to implement a medical workspaces management system 14 that opens and maintains a set of sessions for users (e.g. doctors, nurses, or other medical professionals, where each session manages a plurality of different application program instances 16 for a user), collects location information from a locating service(s) 20 that monitors locations of persons in a monitored space 22 (e.g. encompassing the functional space of the hospital or other medical facility) and tracks dynamic events such as movement of doctors, hospital shift changes, and so forth. The medical workspaces management system 14 applies one or more sets of rules to prioritize various events in order to decide content to be displayed on various medical content presentation devices (e.g. an illustrative bedside patient monitor 30, an illustrative electronic whiteboard 32, and/or so forth). Software drivers 34, 36 are installed on the various respective medical content presentation devices 30, 32 to interface with the central server 10 to display content pushed to the devices 30, 32 by the central server 10, and to convey user inputs, e.g. received via a user's mobile device 38 (such as a cellphone, tablet computer, or so forth) back to the central server 10. For a medical content presentation device such as the illustrative bedside patient monitor 30 which has a display 40 with a relatively small display area, the rules preferably present a single tile or window with the most important content as determined by the prioritization rules. On the other hand, for a medical content presentation device such as the illustrative electronic whiteboard 32 which has a display 42 with a relatively large display area, the rules optionally present a plurality of tiles or windows (illustrative three tiles or windows 44) which may contain content of different users or different types of content (e.g. content of different applications) for a single user, and focused on the exact patient in the room.

The illustrative server computer 10 is shown as a single server; however, it is to be appreciated that the server computer may be a plurality of networked computers, e.g. an ad hoc network of computers sometimes referred to as a cloud computing resource. The non-transitory storage medium 12 storing the instructions that are read and executed by the server computer 10 to implement the medical workspaces management system 14 (and optionally also the various managed application program instances 16) may be a hard drive or plurality of hard drives (e.g. RAID) or other magnetic storage medium, a solid state drive (SSD) or other electronic storage medium, an optical disk or other optical storage medium, various combinations thereof, or so forth. Moreover, the non-transitory storage medium 12 may be directly connected with or integral with the server computer 10 (e.g. an internal hard drive or external hard drive connected by a USB cable or other connection) or may be connected via a wired, wireless, or hybrid electronic network (e.g. a wired and/or wireless Ethernet, WiFi, the Internet, various combinations thereof, or so forth). Data communication between the server computer 10 and the various medical content presentation devices 30, 32 may be via a wired, wireless, or hybrid electronic network (e.g. a wired and/or wireless Ethernet, WiFi, the Internet, various combinations thereof, or so forth).

The associated locating service(s) 20 may employ a real-time locating service (RTLS), swipe card technology, and/or other technologies to locate persons and mobile equipment with varying temporal and spatial granularities. By way of non-limiting illustration, some examples of locating service technologies include RTLS employing RFID tags worn by medical personnel and detected by RFID tag readers positioned at strategic locations around the monitored space 22; the use of swiped or chipped ID cards that medical personnel use to clock in or out of service; proximity sensors employing infrared, ultrasound, or other proximity detection or measurement technology installed on or with one or more of the various medical content presentation devices 30, 32 to measure proximity of medical personnel to the device; video-based facial recognition, retina scanners, or other biometric devices for identifying medical personnel by reading biometric data of the persons; GPS-based tracking using GPS capability of mobile devices 38 issued to medical personnel; WiFi access point (AP) based locating technologies leveraging signal strength of WiFi connections with such mobile devices 38; various combinations thereof; or so forth. It will be appreciated that the spatial and temporal resolution or granularity of the locating service(s) 20 depends upon the choice of locating technology or technologies, and moreover may be non-uniform throughout the monitored space 22 (e.g. may have finer granularity in patient rooms versus in hospital corridors).

Advantageously, the disclosed approaches place much of the data processing and computational tasks at the server computer 10 which can be designed to have large computational capacity. By contrast, the various medical content presentation devices 30, 32 perform less computationally demanding tasks such as running the various drivers 34, 36 to receive and display medical content and to detect user inputs and send these inputs to the server computer 10. However, it is contemplated to distribute more of the computational tasks to the various medical content presentation devices 30, 32, e.g. the server 10 may convey vital sign data that is transformed into trend lines or other display content by software executing on the various medical content presentation devices 30, 32 (e.g. by way of microprocessors or microcontrollers of these devices). Moreover, while it has been mentioned that the users' mobile devices 38 may be used as input devices (if the user is authenticated on the mobile device), which has the advantage of the supplied user credentials and inputs being uniquely associated with the respective users, various user inputs may additionally or alternatively be supplied by controls (e.g. buttons, keyboard, et cetera) built into the various medical content presentation devices 30, 32.

The disclosed medical workspaces management approaches advantageously provide clinically relevant information across disparate sources and in a clinically meaningful way, based on rules which can share patient context, share specific caregiver workflow state, track user location, focus, and proximity to the display technology in question, and track patient clinical state as well as situational awareness.

Figure 2:
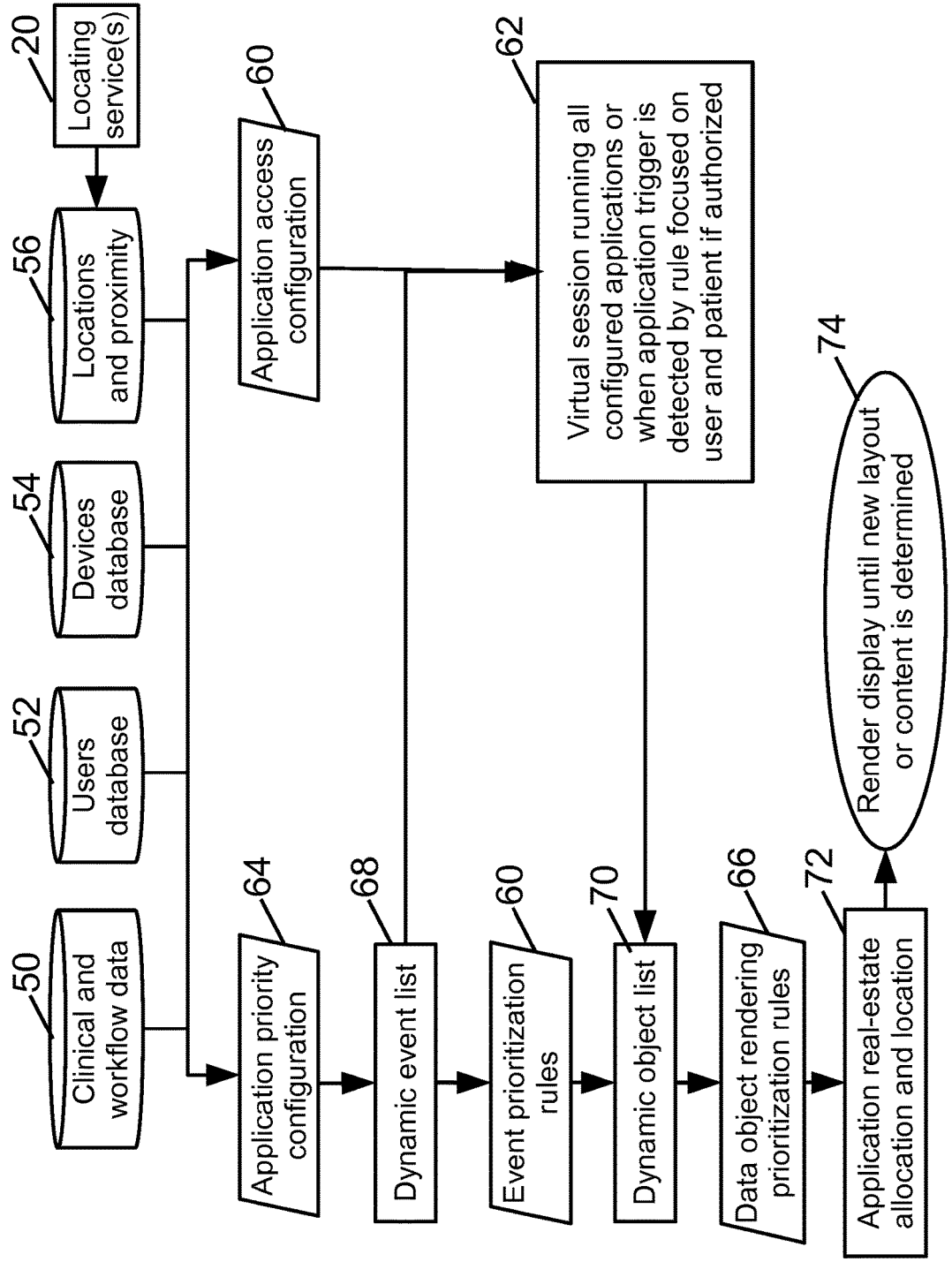
FIG. 2 shows an illustrative embodiment of the medical workspaces management system of FIG. 1.

With reference to FIG. 2, an illustrative implementation of the medical workspaces management system 14 of FIG. 1 is diagrammatically shown and here described. The medical workspaces management system 14 receives data from various data sources. For example, an illustrative non-transitory storage medium 50 stores clinical patient data, patient admissions data, and workflow data. This may include, by way of non-limiting illustration, one or more of: a HIS, PACS, CVIS, or other patient data storage containing medical data such as test results, vital sign data, physician examination reports, and so forth; information on medical personnel shift schedules or other work schedules; a hospital admissions database storing information such as patient identification information, hospital room/bed assignments, or so forth; and the like. A non-transitory storage medium 52 stores a users' database suitably containing information such as user identification information, user authorization information such as a passwords, biometric signatures, or the like; medical role information such as medical specialty or specialties, professional level (e.g. doctor, nurse, therapist, et cetera); and so forth. A non-transitory storage medium 54 store a devices database suitably containing information on the various medical content presentation devices 30, 32 distributed throughout the hospital. This information may include, for example: location of each device in the monitored space 22 (this may be updated in real time via an RTLS component of the locating service(s) 20 in the case of mobile devices, e.g. by tracking attached RFID tags), device capabilities or characteristics such as display size, display resolution and type (color versus monochrome, for example), audio capability, whether the device includes a proximity sensor, processing capability of each device, information on the installed drivers 34, 36, et cetera. A non-transitory storage medium 56 stores location and optional proximity data for users (and optionally also for patients, and/or optionally for medical devices as monitored by the locating service(s) 20). It will be appreciated that the storage configuration shown in FIG. 2 is merely an illustrative example, and more generally various types of data may be variously distributed amongst the various storage media and/or databases; moreover, while separate storage media are illustrated the various databases may be variously collectively stored on common storage media or alternatively may be distributed across different storage media.

With continuing reference to FIGS. 1 and 2, an illustrative embodiment of the medical workspaces management system 14 is diagrammatically depicted. An application access configuration 60 provides for creating a virtual session 62 including running instances 16 of a plurality of medical applications on the server computer 10 with the instances associated with the authenticated user. In one suitable implementation, the application access configuration 60 includes a listing of all external applications and scripts/command line interface/uniform resource locator (URL) addresses, or so forth to programmatically pass user and patient context in for single sign-on. Some application do not require authenticated user or user roles in order to present data, while others do. Some applications are queued based on clinical user role and not specifically the user. An example is that the ventilator interface display which may be set up to be active if a respiratory therapist is present but not if a visitor is present. The configuration 60 further may include mapping of clinical data, workflow, and proximity information (orders, planned interventions), to a common semantic and nomenclature execution system. This supports data-triggered rule authoring. For example, a rule set 64 implements a hierarchical events and application prioritization based on available data and attendance information. Attendance is suitably defined as the set of users (whose information is in the users database 52) and other persons (not in the users database 52) in a defined proximity of the medical content presentation device 30, 32 whose content to be presented is generated by the medical workspaces management system 14. The term "proximity" and similar nomenclature in this context can be variously defined, e.g. as a fixed distance (within 5 meters of the presentation device) or based on architectural considerations (e.g. located in the same room that contains the presentation device). The locating services 20 (e.g. an optional proximity sensor built into the presentation device) can also optionally measure distance between the user and the presentation device to optimize display aspects for distance. For example, if the user is further away from the display, the critical information is rendered in a surrogate application so the information can be rendered for the user to consume. As an example, data object rendering prioritization rules 66 to determine the content of the instances to be presented may include rules for determining at least one of an amount of content to be presented and a font size for textual content to be presented based on the determined distance between the user and the presentation device.

The application priority configuration rules 64 output a dynamic event list 68 which is then run through the data object rendering rule set 60 to produce a dynamic object list 70, where each application object is assigned a relative weighting as to clinical usefulness and rendering capabilities for consideration in the aggregate of the rest of the events and applications. "Usefulness" is based on current clinical context, patient state (e.g. sleeping), and severity of the information to be displayed (e.g. high priority physiologic alarm). This criteria also takes into consideration the number and/or medical roles of the users in attendance in the display domain at the current time, and optionally also their relative proximity to the display at the level of the object rendering rules 66.

In a real-estate allocation and location process 72, based on the configured display technology (e.g. retrieved from the devices database 54), application priority/capabilities 64, and current dynamic event list 68. This step 72 optimizes the application sizing so if an application cannot be rendered in a readable way from across the room the important information is extracted and rendered in a surrogate object.

The medical workspaces management system 14 is activated when a known patient is present in the display domain of the presentation device. In one example, the patient is admitted to the room where a large electronic white board or other flat panel display 32 is installed. Here the patient focus is bound to the available application asset. Applications that do not require authenticated user information are rendered per rules application which require user log-on are triggered when an authorized user is in the location domain of the display. In some cases the display is based on the presence of a visitor (non-caregiver not included in the users database 52) rather than a caregiver (i.e. a user in the users database 52). Once a user is recognized in the display domain, the rest of the applications requiring user or role based authentication are active. This creates a new dynamic event list 68 available to the system. As new clinical data, schedule information, patient results and users change the system recalculates the optimal data presentation based on current events and user proximity as determined from the locating service(s) 20. Supervisory rules check for user dwell time and context changes to prevent display thrashing and keep updates limited to a usable rate (e.g. four times a minute). The display is rendered in operation 74 until a new layout or content is determined.

The phrase "presentation of content at the medical content presentation device" or similar phraseology encompasses any presentation of the content in a human-perceptible fashion. Typically, the presentation of content is by display of the content on a display of the presentation device. However, presentation may additionally or alternatively include presenting the content aurally using electronic speech synthesis or playback of pre-recorded voice recording, presentation by illuminating an LED indicator or the like designed to represent (a portion of) the content to be presented, or so forth.

Figure 3:
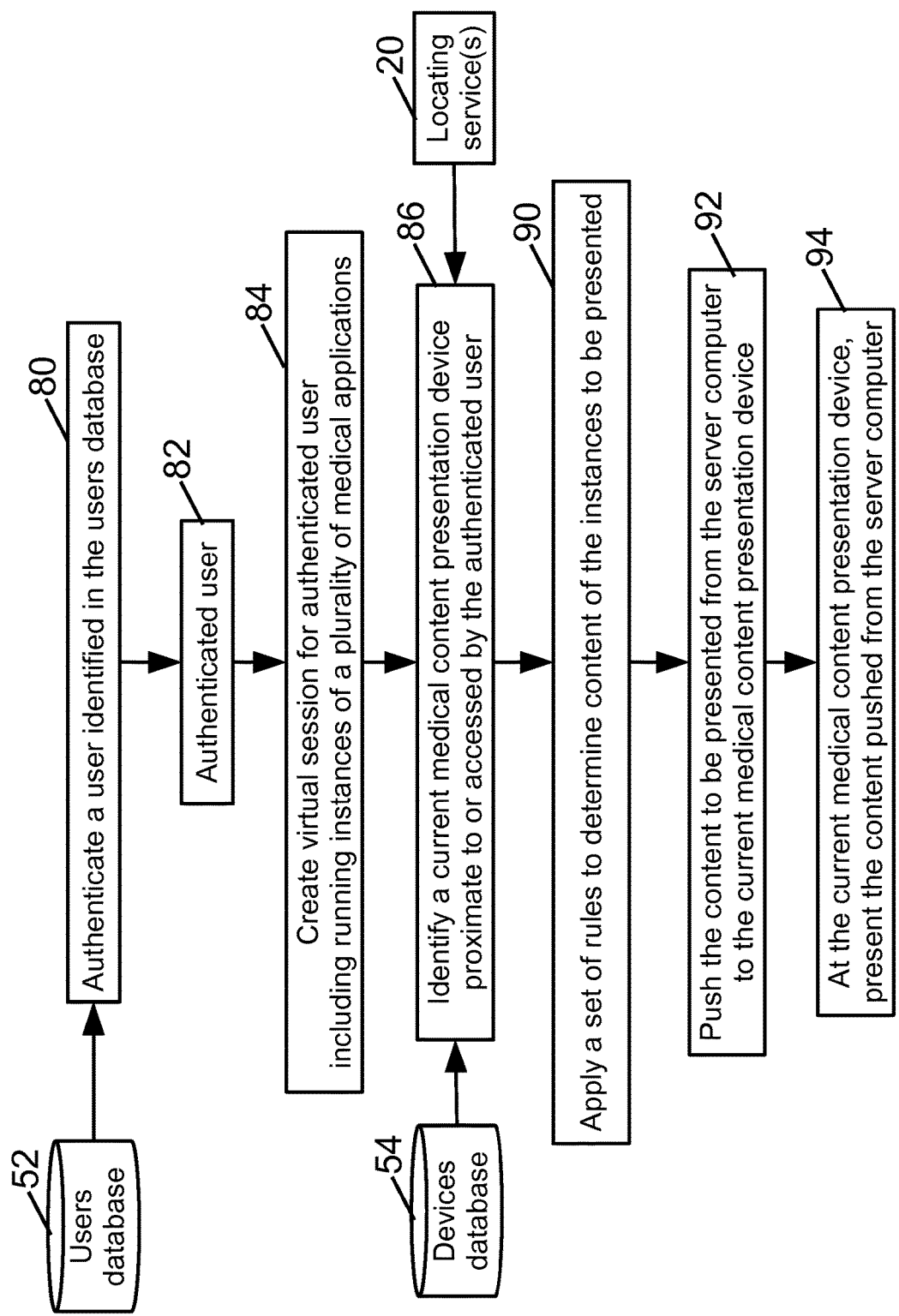
FIG. 3 shows an illustrative medical workspaces management method embodiment suitably performed by the medical workspaces management system of FIGS. 1 and 2.

With reference to FIG. 3, an illustrative medical workspaces management method suitably performed by the medical workspaces management system 14 of FIGS. 1 and 2 is described. In an operation 80, a user identified in the users database 52 is authenticated by the server computer 10 so as to become an authenticated user 82. This may employ receiving information from the use, e.g. a password, or action by the user such as swiping a swipe card or inserting a chipped card at a check-in card reader. In some embodiments, the authentication 80 may require a two-factor or multi-factor authentication, and/or may utilize the reading of a biometric signature (e.g. the user inserts a finger into a fingerprint reader, or gazes into a retina scanner, et cetera) or so forth. In an operation 84 performed by the server computer 10, a virtual session is created, which includes running instances 16 of a plurality of medical applications on the server computer 10 with the instances associated with the authenticated user. Preferably, the user does not need to be individually authenticated on each such application. Rather, the authentication provided in the operation 80, once complete, serves as the authentication for the individual medical applications. Thus, in such embodiments the creating of the virtual session 84 is performed after completion of the authenticating 80 and does not include receiving authentication information from the authenticated user and does not include detecting an authentication action by the authenticated user.

In an operation 86, a current medical content presentation device is identified, for example based on proximity to the authenticated user, or because the authenticated user has logged into the current presentation device. In proximity-based device identification, an RTLS component of the locating service(s) 20 is suitably used to track the current location of the authenticated user (for example, the authenticated user may wear an RFID tag that is tracked by strategically placed RFID readers). Locations of the presentation devices may be stored in the devices database 54, or may be tracked by the RTLS 20, e.g. using RFID tags attached to the devices, or may be tracked using video based technology mounted on the display device. In embodiments in which attendance is leveraged in determining the content to be presented (e.g., so as to provide contextually relevant content such as patient status information during shift changes, content relevant to the specialty or specialties of users in attendance, non-medical content in cases where visitors are in attendance, or so forth), the operation 86 suitably further uses the RTLS component of the locating service(s) 20 to track locations of the other users in the users database 52 and/or to track locations of other persons not in the users database 52 (and hence presumed to be visitors).

In an operation 90, a set of rules is applied to determine content of the application instances 16 to be presented. Some rules may be clinical in nature. For example, if the patient is detected o have a cardiac problem that requires the Cath lab, the rule will cause the current Cath lab schedule to be brought up. In general, to apply the clinically-based rules, a current patient is identified based on proximity, as determined by the at least one locating service 20, of the current patient to the current location of the authenticated user. At least one rule of a clinical rule then operates on the identification of the current patient to determine the content of the instances to be presented as content relating to the current patient. Some rules may operate at least in part on the current attendance as described previously, e.g. based on the medical roles of the current attendance as indicated in the users database 52. If the tracking includes determining a distance between the current location of the authenticated user and the current medical content presentation device, then the set of rules may determine at least one of an amount of content to be presented and a font size for textual content to be presented based on the determined distance. Similar (and possibly in conjunction with this distance-adjustment) the display size of the current medical content presentation device may be determined (e.g. by accessing such information stored in the devices database 54 or by querying the device directly) and the set of rules may then operate at least on part on the display size (e.g., more content can be displayed on a larger display).

In the case of a larger display such as the illustrative whiteboard 32, the set of rules may allow for (and mediate between) displaying content of two (or more) authenticated users. In the case of two users, a second user identified in the users database 52 is authenticated via operation 80 whereby the second user becomes a second authenticated user. A second virtual session is created as per operation 84 including running further instances of a plurality of medical applications on the server computer 10 with the further instances associated with the second authenticated user. (Note that the second authenticated user may have access to a different plurality of applications compared with the first authenticated user, possibly with some overlap). The current medical content presentation device is identified as per operation 86 as being proximate to (or accessed by) both the authenticated user and the second authenticated user. In this case, the set of rules is applied determine content of the instances associated with the first authenticated user to be presented and further content of the further instances associated with the second authenticated user to be presented. In one approach, the pushing includes pushing the content to be presented from the server computer 10 to the current medical content presentation device for presentation in a first window or tile displayed on the current medical content presentation device and pushing the further content (of the second user) to be presented from the server computer 10 to the current medical content presentation device for presentation in a second window or tile also displayed on the current medical content presentation device. If a smaller display is available (e.g. the bedside monitor display 40) then the set of rules suitably includes prioritization rules for prioritizing for display content of the instances of the first authorized user versus content of the further instances of the second authorized user.

While leveraging the RTLS 20 provide for automated generation of the content display, in another embodiment the operation 86 identifies the current medical content presentation device by receiving notice from that presentation device that the authenticated user has logged into the presentation device. This approach does not require an RTLS, but has the disadvantage that the user must log onto each presentation device to be used (unless it does not require user log-in).

After the set of rules is applied in the operation 90 to determine the content of the application instances to be presented, this content is pushed in an operation 92 from the server computer 10 to the current medical content display device (for example, over a hospital data network, e.g. an Ethernet or WiFi), and in an operation 94 performed by the presentation device the pushed content is presented (e.g. displayed on the presentation device display).

In addition to presenting pushed content, the current medical content presentation device may also convey user inputs received at the presentation device to the server computer 10. For example, as already mentioned the user may employ a cellphone, tablet computer, or other mobile device 38 with wireless communication capability (e.g. Bluetooth™) to provide such inputs, or may directly interact with user controls of the presentation device such as buttons, a touchscreen, or so forth. In such cases, the server computer 10 forwards the received user inputs to one or more instances that generate the content being presented, thereby enabling the medical application to act on the user input.

Although not explicitly shown in FIG. 3, it will be appreciated that as the doctor or other authenticated user moves about the medical facility within the monitored space 22, for example on rounds to see patients, that the operation 86 will be applied successively (e.g. every minute, or every three minutes, or so forth) so that the current medical content presentation device is updated according to the movements of the doctor. Thus, for example, referring to FIG. 1, if the doctor is initially in the patient room containing the bedside monitor 30 then the bedside monitor 30 is initially the current presentation device. If the doctor then leaves the patient room and enters a conference room containing the electronic whiteboard 32 then the operation 86 updates the current presentation device based on the new current location of the doctor to be the whiteboard 32. Likewise, if the operation 86 uses the RTLS component of the locating service(s) 20 to monitor attendance then as doctors, nurses, specialists, or other users enter or leave the patient's room (again using the patient's room as the authenticated user's current location) the attendance is updated accordingly and the set of rules may adjust the content based on the updated attendance. Thus, for example, if a pulmonologist is initially in attendance then the pushed content may include respiratory content; when the pulmonologist leaves then the respiratory content may no longer be displayed.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A non-transitory storage medium storing instructions readable and executable by a central server computer to perform a medical workspaces management method, comprising:

authenticating, by the central server computer, a user identified in a users database whereby the user becomes an authenticated user;

opening and maintaining, by the central server computer, a virtual session including running instances of a plurality of medical applications on the central server computer with the instances associated with the authenticated user;

identifying a current medical content presentation device proximate to or accessed by the authenticated user;

applying, by the central server computer, a set of rules to prioritize dynamic events in order to determine content of the instances to be presented, wherein the applying of the set of rules includes applying at least one clinical rule operating on an identification of a current patient to determine the content of the instances to be presented as content relating to the current patient; and pushing the content to be presented from the central server computer to the current medical content presentation device for presentation at the current medical content presentation device.

2. The non-transitory storage medium of claim 1, wherein the identifying comprises:

tracking a current location of the authenticated user using at least one locating service; and identifying the current medical content presentation device based on proximity of the current location of the authenticated user to the current medical content presentation device.

3. The non-transitory storage medium of claim 2, wherein the identifying further comprises:

concurrently tracking current locations of other users in the users database besides the authenticated user using a real-time locating service (RTLS) component of the at least one locating service; and determining a current attendance from the concurrent tracking wherein the current attendance includes the authenticated user and one or more users besides the authenticated user who are proximate to the medical content presentation device;

wherein the set of rules to determine the content of the instances to be presented rules operates at least in part on the current attendance.

4. The non-transitory storage medium of claim 3, wherein the set of rules to determine the content of the instances to be presented operates at least in part on one or more medical roles of the current attendance determined from the users database.

5. The non-transitory storage medium of claim 3, wherein:

the concurrent tracking further includes concurrently tracking locations of persons who are not in the users database using the RTLS component of the at least one locating service; and the current attendance further includes one or more persons who are not in the users database and who are proximate to the medical content presentation device.

6. The non-transitory storage medium of claim 2, wherein:

the tracking of the current location of the authenticated user using the at least one locating service includes determining a distance between the current location of the authenticated user and the current medical content presentation device using a proximity sensor; and the set of rules to determine the content of the instances to be presented includes determining at least one of an amount of content to be presented and a font size for textual content to be presented based on the determined distance.

7. The non-transitory storage medium of claim 2, wherein:

the identifying of the current medical content presentation device includes identifying a display size of the current medical content presentation device; and the set of rules operates at least on part on the display size.

8. The non-transitory storage medium of claim 2, wherein the medical workspaces management method further comprises:

identifying, by the at least one locating service, a current patient based on proximity of the current patient to the current location of the authenticated user;

wherein the applying of the set of rules includes applying at least one clinical rule operating on the identification of the current patient to determine the content of the instances to be presented as content relating to the current patient.

9. The non-transitory storage medium of claim 1, wherein the medical workspaces management method further comprises:

authenticating a second user identified in the users database whereby the second user becomes a second authenticated user;

creating a second virtual session including running further instances of a plurality of medical applications on the central server computer with the further instances associated with the second authenticated user;

identifying the current medical content presentation device as proximate to or accessed by both the authenticated user and the second authenticated user;

wherein the applying of the set of rules determines the content of the instances to be presented and further content of the further instances to be presented; and wherein the pushing includes pushing the content to be presented from the central server computer to the current medical content presentation device for presentation in a first window or tile displayed on the current medical content presentation device and pushing the further content to be presented from the central server computer to the current medical content presentation device for presentation in a second window or tile also displayed on the current medical content presentation device.

10. The non-transitory storage medium of claim 1, wherein the identifying comprises:

receiving notice from the current medical content presentation device indicating the authenticated user has logged into the current medical content presentation device.

11. The non-transitory storage medium of claim 1, wherein the medical workspaces management method further comprises:

receiving user inputs from the current medical content presentation device and forwarding, by the central server computer, the user inputs to one or more instances generating the content of the instances to be presented.

12. The non-transitory storage medium of claim 1, wherein:

the authenticating includes at least one of receiving authentication information from the user or detecting an authentication action by the user; and the creating of the virtual session is performed after completion of the authenticating and does not include receiving authentication information from the authenticated user and does not include detecting an authentication action by the authenticated user.

13. A medical workspaces management device, comprising:

a central server computer; and a non-transitory storage medium storing instructions readable and executable by the central server computer to perform a medical workspaces management method including:

authenticating, by the central server computer, a user identified in a users database whereby the user becomes an authenticated user;

after completion of the authenticating, opening and maintaining, by the central server computer, a virtual session including running instances of a plurality of medical applications on the central server computer with the instances associated with the authenticated user;

tracking a current location of the authenticated user using at least one locating service;

identifying a current medical content presentation device based on proximity of the current location of the authenticated user to the current medical content presentation device;

applying, by the central server computer, a set of rules to prioritize dynamic events in order to determine content of the instances to be presented, wherein the applying of the set of rules includes applying at least one clinical rule operating on an identification of a current patient to determine the content of the instances to be presented as content relating to the current patient; and pushing the content to be presented from the central server computer to the current medical content presentation device for presentation at the current medical content presentation device.

14. The medical workspaces management device of claim 13, wherein the medical workspaces management method further comprises:

identifying, by the at least one locating service, a current patient based on proximity of the current patient to the current location of the authenticated user;

wherein the applying of the set of rules includes applying at least one clinical rule operating on the identification of the current patient to determine the content of the instances to be presented as content relating to the current patient.

15. The medical workspaces management device of claim 13, wherein the identifying further comprises:

concurrently tracking current locations of other users in the users database besides the authenticated user using a real-time locating service (RTLS) component of the at least one locating service and of persons not in the users database; and determining a current attendance from the concurrent tracking wherein the current attendance includes the authenticated user and any user besides the authenticated user who is proximate to the medical content presentation device and any person not in the users database who is proximate to the medical content presentation device;

wherein the set of rules to determine the content of the instances to be presented rules operates at least in part on the current attendance.

16. The medical workspaces management device of claim 15, wherein the set of rules to determine the content of the instances to be presented operates at least in part on one or more medical roles of the current attendance determined from the users database.

17. The medical workspaces management device of claim 13, wherein:

the tracking of the current location of the authenticated user using the at least one locating service includes determining a distance between the current location of the authenticated user and the current medical content presentation device using a proximity sensor; and the set of rules to determine the content of the instances to be presented includes determining at least one of an amount of content to be presented and a font size for textual content to be presented based on the determined distance.

18. The medical workspaces management device of claim 13, wherein the medical workspaces management method further comprises:

authenticating a second user identified in the users database whereby the second user becomes a second authenticated user;

creating a second virtual session including running further instances of a plurality of medical applications on the central server computer with the further instances associated with the second authenticated user; and identifying the current medical content presentation device as proximate to or accessed by both the authenticated user and the second authenticated user;

wherein the set of rules includes prioritization rules for prioritizing for display content of the instances versus content of the further instances.

19. The medical workspaces management device of claim 13, further comprising:

a plurality of medical content presentation devices including the current medical content presentation device, wherein each medical content presentation device includes a driver programming the medical content presentation device to receive and present content pushed from the central server computer.

20. A medical workspaces management method, comprising:

at a central server computer, authenticating a user identified in a users database whereby the user becomes an authenticated user;

at the central server computer, opening and maintaining a virtual session including running instances of a plurality of medical applications on the central server computer with the instances associated with the authenticated user;

using at least one locating service, identifying a current medical content presentation device proximate to the authenticated user;

at the central server computer, applying a set of rules to prioritize dynamic events in order to determine content of the instances to be presented, wherein the applying of the set of rules includes applying at least one clinical rule operating on an identification of a current patient to determine the content of the instances to be presented as content relating to the current patient;

pushing the content to be presented from the central server computer to the current medical content presentation device; and at the current medical content presentation device, presenting the content pushed from the central server computer on a display of the current medical content presentation device.

21. The medical workspaces management method of claim 20, wherein the identifying further comprises:
using a real time locating service (RTLS) component of the at least one locating service, concurrently tracking current locations of other users in the users database besides the authenticated user using the RTLS and of persons not in the users database; and
determining a current attendance from the concurrent tracking wherein the current attendance includes the authenticated user and any user besides the authenticated user who is proximate to the medical content presentation device and any person not in the users database who is proximate to the medical content presentation device;
wherein the set of rules to determine the content of the instances to be presented operates at least in part on the current attendance.

22. The medical workspaces management method of claim 21, wherein the set of rules to determine the content of the instances to be presented operates at least in part on one or more medical roles of the current attendance determined from the users database.

23. The medical workspaces management method of claim 20, further comprising:
authenticating a second user identified in the users database whereby the second user becomes a second authenticated user;
creating a second virtual session including running further instances of a plurality of medical applications on the central server computer with the further instances associated with the second authenticated user;
identifying the current medical content presentation device as proximate to or accessed by both the authenticated user and the second authenticated user;
wherein the applying of the set of rules determines content of the instances to be presented and further content of the further instances to be presented; and
wherein the pushing includes pushing the content to be presented from the central server computer to the current medical content presentation device for presentation in a first window or tile displayed on the current medical content presentation device and pushing the further content to be presented from the central server computer to the current medical content presentation device for presentation in a second window or tile also displayed on the current medical content presentation device.

24. The medical workspaces management method of claim 20, wherein:
the authenticating includes at least one of receiving authentication information from the user or detecting an authentication action by the user; and
the creating of the virtual session is performed after completion of the authenticating and does not include receiving authentication information from the authenticated user and does not include detecting an authentication action by the authenticated user.

25. The medical workspaces management method of claim 20, further comprising:
identifying, by the at least one locating service, a current patient based on proximity of the current patient to the current location of the authenticated user;
wherein the applying of the set of rules includes applying at least one clinical rule operating on the identification of the current patient to determine the content of the instances to be presented as content relating to the current patient.

26. The non-transitory storage medium of claim 1, wherein the dynamic events comprise a movement of the authenticated user or a shift or schedule change for the authenticated user.

* * * * *